United States Patent

Cano et al.

[11] Patent Number: 5,779,716
[45] Date of Patent: Jul. 14, 1998

[54] DEVICE FOR REMOVING SOLID OBJECTS FROM BODY CANALS, CAVITIES AND ORGANS

[75] Inventors: Gerald G. Cano, Penn Hills; Robert W. Doebler, Sewickley, both of Pa.

[73] Assignee: Metamorphic Surgical Devices, Inc., Pittsburgh, Pa.

[21] Appl. No.: 539,875

[22] Filed: Oct. 6, 1995

[51] Int. Cl.⁶ .......................................... A61B 17/22
[52] U.S. Cl. .......................... 606/114; 606/113; 606/127; 606/110
[58] Field of Search ................... 606/110, 113, 606/114, 127; 600/37

[56] References Cited

U.S. PATENT DOCUMENTS

| | | | |
|---|---|---|---|
| 4,665,906 | 5/1987 | Jervis | 128/92 |
| 5,067,957 | 11/1991 | Jervis | 606/108 |
| 5,147,371 | 9/1992 | Washington et al. | 606/127 |
| 5,188,111 | 2/1993 | Yates et al. | 128/657 |
| 5,190,542 | 3/1993 | Nakao et al. | 606/47 |
| 5,190,546 | 3/1993 | Jervis | 606/78 |
| 5,190,555 | 3/1993 | Wetter et al. | 606/114 |
| 5,192,284 | 3/1993 | Pleatman | 606/114 |
| 5,192,286 | 3/1993 | Phan et al. | 606/127 |
| 5,201,741 | 4/1993 | Dulebohn | 606/113 |
| 5,215,521 | 6/1993 | Cochran et al. | 604/22 |
| 5,234,439 | 8/1993 | Wilk et al. | 606/114 |
| 5,279,539 | 1/1994 | Bohan et al. | 600/37 |
| 5,312,416 | 5/1994 | Spaeth et al. | 606/110 |
| 5,312,417 | 5/1994 | Wilk | 606/114 |
| 5,341,815 | 8/1994 | Cofone et al. | 128/749 |
| 5,352,184 | 10/1994 | Goldberg et al. | 600/37 |
| 5,354,303 | 10/1994 | Spaeth et al. | 606/128 |
| 5,366,460 | 11/1994 | Eberbach | 606/151 |
| 5,368,597 | 11/1994 | Pagedas | 606/114 |
| 5,480,404 | 1/1996 | Kammerer et al. | 606/113 |
| 5,486,182 | 1/1996 | Nakao et al. | 606/114 |
| 5,486,183 | 1/1996 | Middleman et al. | 606/114 |

*Primary Examiner*—Robert A. Hafer
*Assistant Examiner*—Benjamin V. Koo
*Attorney, Agent, or Firm*—Webb Ziesenheim Bruening Logsdon Orkin & Hanson, P.C.

[57] ABSTRACT

The present invention is directed to a surgical instrument used in minimally invasive procedures performed under either direct, endoscopic, fluoroscopic, or other visualization. The present invention is also directed to a method of removing foreign objects from the body with the instrument. The surgical instrument includes a wire linkage and wire frame which can be retracted and extended to form a loop. A mouth of a sack is attached to the loop, said sack being used to encircle and capture foreign objects in body canals, cavities and organs. The wire frame is formed of a shape-memory-effect alloy wire, the alloy in a super elastic state and previously trained to form the loop, the loop forming when the said wire frame is extended beyond the sheath.

23 Claims, 6 Drawing Sheets

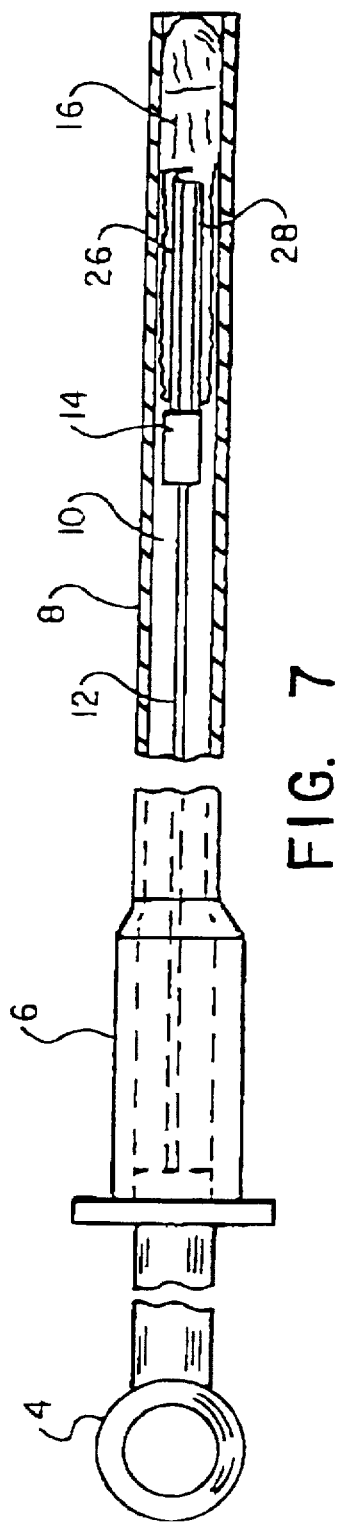
FIG. 7
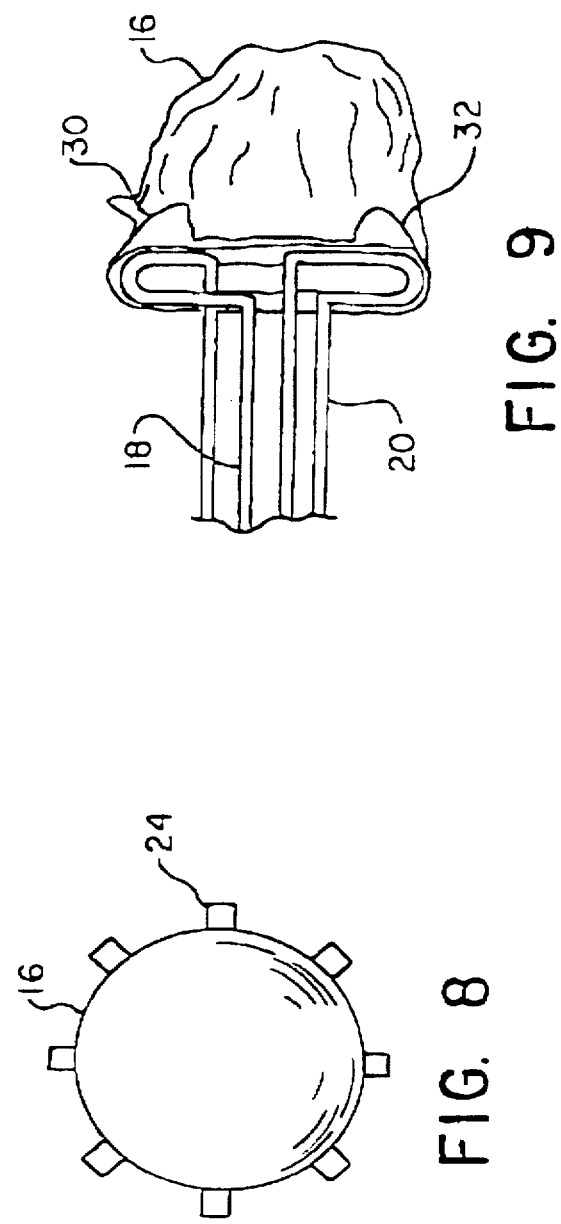
FIG. 9
FIG. 8

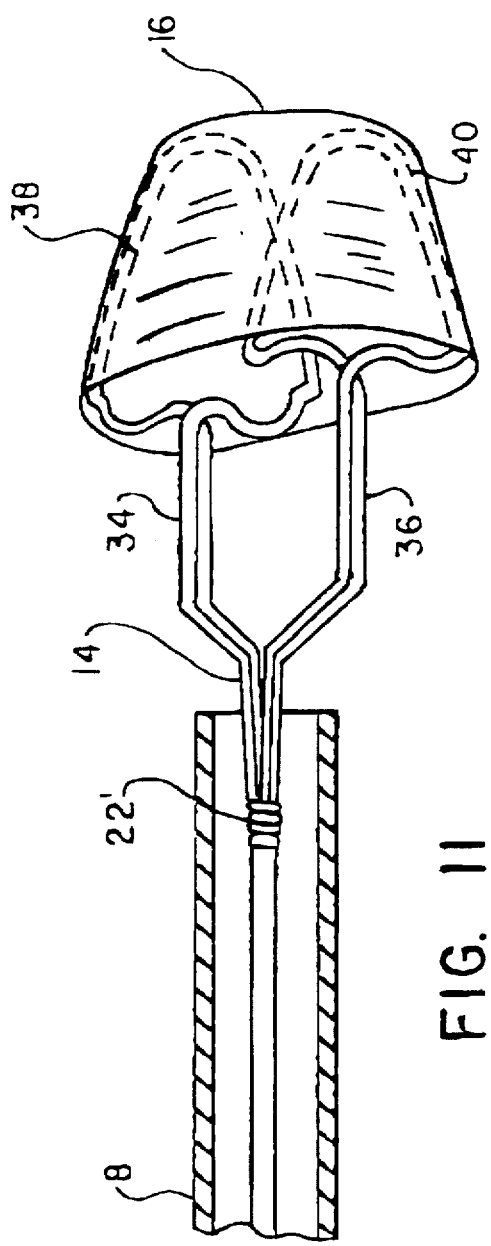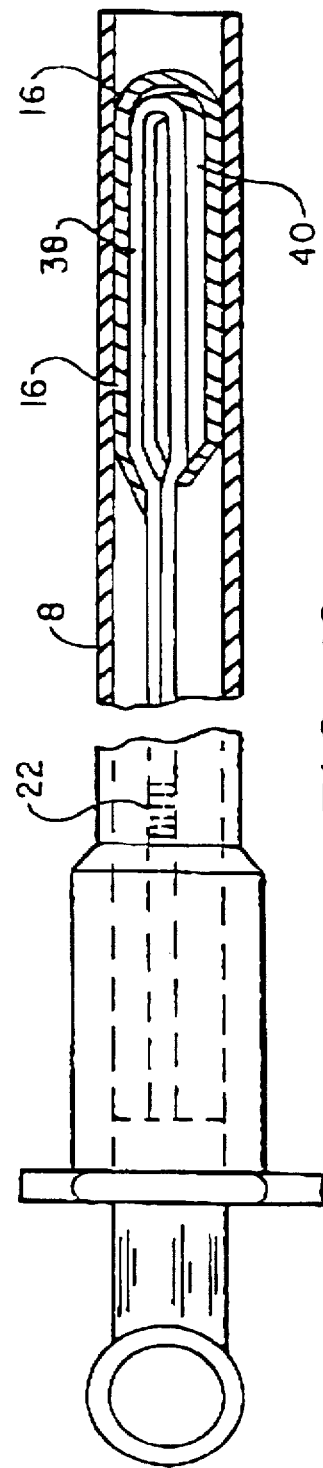

DEVICE FOR REMOVING SOLID OBJECTS FROM BODY CANALS, CAVITIES AND ORGANS

BACKGROUND OF THE INVENTION

1. Field of the Invention

This invention relates generally to surgical instruments used in minimally invasive procedures performed under either direct, endoscopic, fluoroscopic or other visualization. More specifically, the present invention relates to a surgical instrument used to capture and remove foreign objects or excised tissue lodged in body canals, cavities, and organs.

2. Background of the Invention

Existing surgical devices for grasping and removing foreign objects from body organs or cavities may be classified as either mechanically actuated forceps, mechanically actuated snares or mechanically actuated baskets. Each of these classes of devices may be positioned within the body under direct, endoscopic, fluoroscopic or other visualization. Mechanically actuated forceps typically consist of two, three, or four arms or prongs, each arm typically ending with a hooked tip. The arms are typically composed of flat or round stainless steel and are connected at the end opposite the tip to a handle used to position and grasp. Most mechanically actuated forceps include an inner and outer sheath arrangement. The outer sheath is fixed with respect to the handle, while the inner sheath may be advanced from or retracted into the outer sheath. When the inner sheath is retracted within the outer sheath, the arms spread from each other, allowing the forceps to be advanced toward and around the object within the body sought to be captured or removed. The arms of the forceps are then tightly closed about the object by extending the inner sheath from the outer sheath in the direction of the tips, whereupon the arms are pulled together to encircle and grasp the object sought to be captured or removed.

Mechanically actuated snares are typically comprised of a single loop wire enclosed within a sheath, a portion of which can be extended beyond the sheath to form an oval opening. The dimensions of the oval opening are controlled by the length of wire advanced beyond the end of the sheath. After the snare is positioned by the surgeon, a portion of the wire is advanced beyond the end of the sheath until a loop larger than the object is formed. The loop is manipulated by the surgeon, sometimes extensively, until the object is within the plane of the loop. The sheath is then advanced and the wire retracted, so that the loop closes around the object, thus ensnaring it.

Several of the snare-type surgical devices also incorporate a sack associated with the snare to trap the object to be captured or removed. One example includes U.S. Pat. No. 5,190,555 which includes a sack of a flexible material and further requires a drawstring to open and close the sack. Another example is U.S. Pat. No. 5,192,286 which includes a net which can be collapsed to facilitate introduction into the body lumen and opened in situ to permit capture and retrieval of deleterious materials. The net is opened by a flexible loop member. Another example is U.S. Pat. No. 5,354,303 which includes a flexible sac and a resilient or spring loaded rim member disposed about the opening to urge the opening to an open configuration when deployed in the body cavity.

Mechanically actuated baskets are typically comprised of three to six wires enclosed within a sheath. The wires are joined at a first end with a handle. The wires are joined at a second distal end to each other. As the wires are advanced beyond the sheath, a basket forms. The volume of the basket is controlled by the length of wire advanced. The closed basket is positioned relative to the object to be captured or removed, whereupon a portion of the wires is advanced beyond the sheath to form a basket of sufficient volume to enclose the object. The basket is manipulated, sometimes extensively, until the object is within the volume of the basket as defined by the wires. The wires are retracted into the sheath, shrinking the volume and pulling the object against the end of the sheath, thus grasping it for removal. The smaller the object, the more wires are needed to trap and hold the object. Conversely, large stones will not be able to work their way between closely spaced wires for capture.

Surgical instruments of the prior art have important limitations. First, they are mechanically complex, particularly mechanical baskets, and are therefore difficult, time-consuming and expensive to manufacture. Second, they require difficult manipulations by the surgeon to effectively grasp the object to be removed. This is particularly true where the surgical procedure would best be served by a surgical device which could capture or remove objects with a capturing portion which was at a generally perpendicular angle to the longitudinal axis of the surgical device. One example of such a procedure is where the object to be captured or removed is present in a blood vessel or is a kidney stone present in the ureter. None of the prior art devices effectively addresses this type of operation in an effective and efficient manner, as none of the prior art devices has a capturing portion which is generally perpendicular to the longitudinal axis of the surgical device. Such manipulations required by prior art devices extend the duration of the surgery to increase the risk to the patient, forming a third important limitation. Fourth, where wire of sufficient elastic strength to open and close about an object is used, the rigidity of such a wire significantly contributes to the trauma of sensitive tissue surrounding the object to be captured or removed during manipulation by the surgeon.

There is a need in the art for a surgical device capable of capturing and removing objects or excised tissue from body canals, cavities and organs which is not mechanically complex, is easily manipulated during surgery and will not cause significant trauma to sensitive tissue surrounding the object to be captured or removed.

SUMMARY OF THE INVENTION

It is an object of the present invention to provide a surgical device which is easy to position and requires little manipulation to capture a foreign object lodged in body canals, cavities and organs. It is an additional object of the present invention to provide a surgical device which is not mechanically complex and is relatively easy to manufacture. It is a further object of the present invention to provide a surgical device which will not cause significant trauma to sensitive tissue surrounding the object to be captured or removed. It is a further object of the present invention to provide a surgical device capable of capturing or removing objects from body canals, cavities or organs which has a capturing portion at a generally perpendicular angle to the longitudinal axis of the surgical device.

These and other objects are obtained with the present invention which is a surgical instrument for removing foreign objects or excised tissue from body canals, cavities or organs, used in minimally invasive procedures performed under either direct, endoscopic, fluoroscopic or other visualization comprising:

a) a handle, said handle including a means for extending and retracting a wire linkage attached to said handle, said wire linkage having a first proximal end attached to said means for extending and retracting said wire linkage, said wire linkage having a second distal end;

b) an elongated tubular sheath attached to said handle, said sheath having a hollow lumen extending longitudinally therethrough, said wire linkage contained within said lumen, said wire linkage being adapted to slide within said lumen of said sheath;

c) a wire frame attached to said wire linkage at said second distal end of said wire linkage, said wire frame being extendible beyond said sheath and retractable into said sheath by said means for extending and retracting said wire linkage which correspondingly extends and retracts said wire frame within said sheath, said wire frame being formed of a shape-memory-effect alloy wire, said alloy in a super elastic state and previously trained to form a loop, said loop forming when said wire frame is extended beyond said sheath; and d) a sack having a mouth, said mouth of said sack being attached to said wire frame wherein said wire frame opens and closes said mouth of said sack when said wire frame is extended from or retrieved into said sheath.

The present invention also includes a method of removing a foreign object or excised tissue from a body canal, cavity or organ, comprising the steps of:

a) inserting a surgical instrument into said body canal, cavity or organ through an entry point, said entry point including at least one of an existing body opening and a surgically created body opening;

b) viewing the inserting of said surgical instrument through at least one of the group consisting of direct examination, endoscopic examination, or fluoroscopic examination;

c) continuing the inserting of said surgical instrument to a point beyond said foreign object with respect to entry point;

d) extending said surgical instrument to form a sack;

e) withdrawing said surgical instrument to encircle said foreign object within said sack;

f) retracting said surgical instrument to capture said foreign object in said sack;

g) removing said surgical instrument and said foreign object from said body, wherein said surgical instrument includes i) a handle, said handle including a means for extending and retracting a wire linkage attached to said handle, said wire linkage having a first proximal end attached to said means for extending and retracting said wire linkage, said wire linkage having a second distal end;

ii) an elongated tubular sheath attached to said handle, said sheath having a hollow lumen extending longitudinally therethrough, said wire linkage contained within said lumen, said wire linkage being adapted to slide within said lumen of said sheath;

iii) a wire frame attached to said wire linkage at said second distal end of said wire linkage, said wire frame being extendible beyond said sheath and retractable into said sheath by said means for extending and retracting said wire linkage which correspondingly extends and retracts said wire frame within said sheath, said wire frame being formed of a shape-memory-effect alloy wire, said alloy in a super elastic state and previously trained to form a loop, said loop forming when said wire frame is extended beyond said sheath; and iv) a sack having a mouth, said mouth of said sack being attached to said wire frame, wherein said wire frame opens and closes said mouth of said sack when said wire frame is extended from or retrieved into said sheath.

BRIEF DESCRIPTION OF THE DRAWINGS

FIG. 7 is a schematic elevational view of the surgical device of the present invention showing the sack portion of the device retracted into the sheath of the device;

FIG. 8 is an elevational view of the sack of the present invention showing the tabs thereof;

FIG. 9 is a schematic elevational view of the sack of the surgical device of the present invention;

FIG. 11 is a schematic elevational view of the surgical device of the present invention showing a slightly modified loop assembly; and FIG. 12 is a schematic elevational view of the surgical device of the present invention showing the slightly modified loops assembly of FIG. 11 in the tubular sheath.

DETAILED DESCRIPTION OF THE INVENTION

Figure 1:
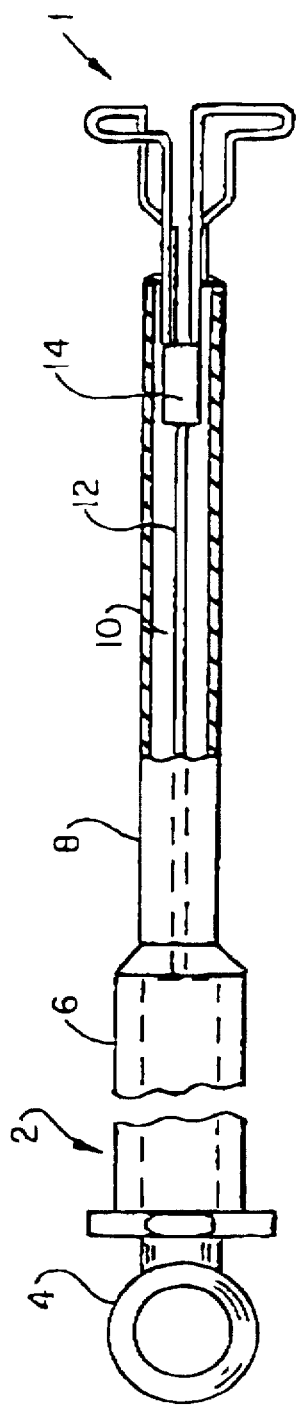
FIG. 1 is a schematic elevational view of the surgical device to remove a foreign object from a body canal, cavity or organ according to the present invention with the wire frame extended from the sheath.
Figure 2:
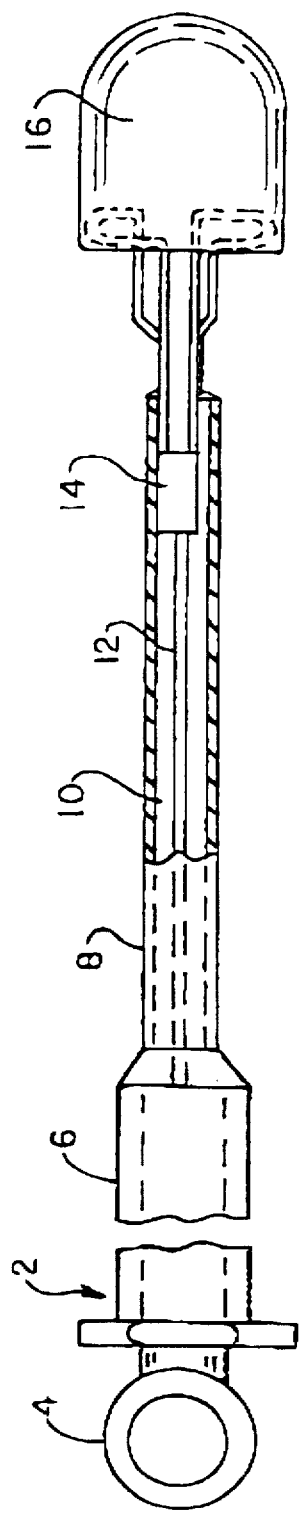
FIG. 2 is a schematic elevational view of the surgical device of the present invention with the wire frame and sack extended from the sheath.

Referring to FIG. 1, a surgical device 1 for capturing and removing foreign objects in organs, canals and cavities in the body according to the teaching of the present invention is shown. Device 1 includes a handle 2 which functions to manipulate the device in the manner set forth below. While the handle may be of any type known in the art, pistol-like grip or syringe-type handles are preferred. Shown in FIG. 1 is a syringe-type handle which includes plunger 4 and cylinder 6. An elongated tubular sheath 8 is attached to cylinder 6 via any means known in the art. Sheath 8 and cylinder 6 cooperate to form lumen 10 therethrough. Sheath 8 can be made of any flexible biocompatible material, including polyethylene, nylon or polyimides. Polyethylene is preferred because its surface has the least friction permitting easy travel of wire linkage 12, wire frame 14 and sack 16 within sheath 8 as explained herein. While polyimides generally have higher dimensional stability, they are less lubricious than polyethylenes. Wire linkage 12 is attached at a first end to plunger 4 and at a second end to wire frame 14. Wire linkage 12 may be a shape-memory-effect alloy in the super elastic state or another biocompatible metal or alloy. Referring to FIG. 2, attached to wire frame 14 is sack 16 which operates to capture foreign objects from body canals, cavities and organs in the manner described below.

Figure 3:
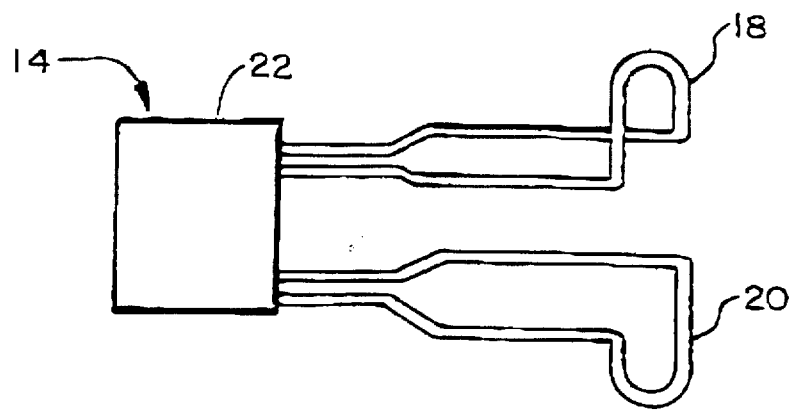
FIG. 3 is a schematic elevational view showing the construction of the two halves of the wire frame in their deployed state.

Referring to FIG. 3, wire frame 14 is shown. Wire frame 14 further includes a half frame 18, a half frame 20 and a junction 22. Junction 22 functions to join and maintain the relative orientations of half frames 18 and 20. Junction 22 is preferably a crimp composed of a biocompatible material. Half frames 18 and 20 are shown in FIG. 3 in their deployed state, wherein at least a portion of each half frame is oriented generally perpendicular to the longitudinal axis of wire linkage 12, as shown in FIGS. 1 and 2. Alternatively, referring to FIGS. 4 and 5, half frame 18 and half frame 20 are shown in their retracted state, wherein it will be seen that each half frame forms a respective loop in a plane substantially parallel to the longitudinal axis of wire linkage 12.

Figure 4:
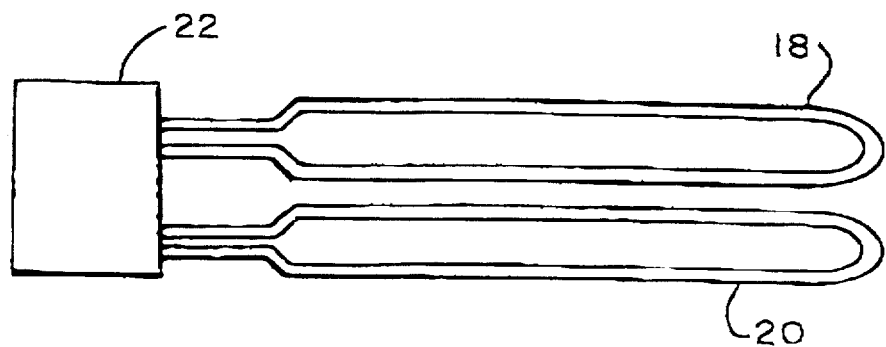
FIG. 4 is a schematic elevational view showing the construction of the two halves of the wire frame in their retracted state.
Figure 5:
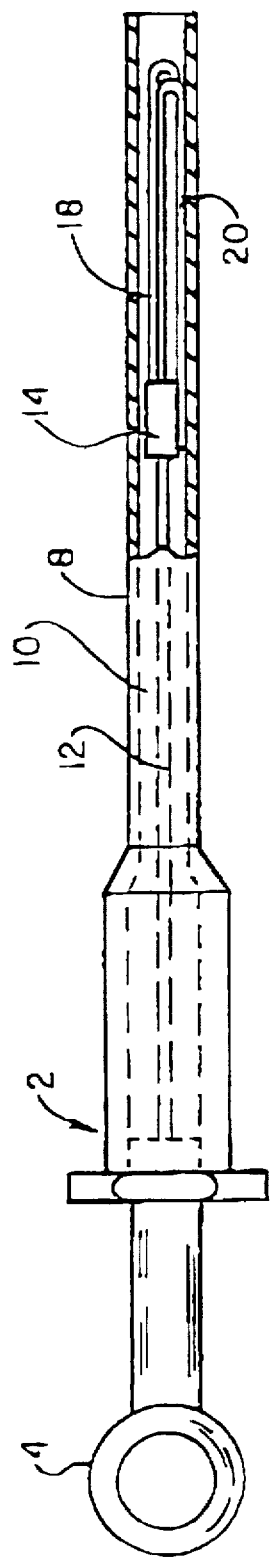
FIG. 5 is a schematic elevational view of the joined wire frame halves retracted in the sheath to form a pair of loops.

Half frame 18 and half frame 20 are each constructed of a shape-memory-effect alloy in the super elastic state. An example of such a shape-memory-effect alloy is Nitinol. Nitinol is a registered trademark assigned to Minnesota Mining and Manufacturing Company of Saint Paul, Minn. Each half frame has been "trained" to form the perpendicular portions described above by the processes known in the art with respect to shape-memory-effect alloys. When the two half frames 18 and 20 are retracted into the sheath 8, they are mechanically stressed within their elastic limits to each form a long narrow loop, the axis of each loop substantially parallel to the longitudinal axis of wire linkage 12 as shown in FIGS. 4 and 5.

Additionally, the shape-memory-effect alloy provides two important benefits. First, due to its ability to "learn" a given shape, it is possible to obtain the perpendicular portions described above which, in turn, facilitates use of the surgical device of the present invention in body lumens and canals. The expansion of the half frames 18 and 20 within a body lumen essentially provides a capturing opening or mouth in sack 16 which is coextensive with the diameter of the lumen, assuring complete capture. This is particularly valuable where the object to be captured or removed is given to fragmentation. The second important benefit of the shape-memory-effect alloy is that it will obtain the desired shape with a minimum of force, remaining firm but pliable, unlike prior art devices made of extremely rigid elastic or spring steel. The pliable yet firm nature of the shape-memory-effect alloy produces either no, or at least far less, trauma to the tissues surrounding the object to be captured or removed as the shape-memory-effect alloy is able to displace soft tissues as necessary, but is pliable to allow for significant back pressure from such soft tissues. In contrast, formed elastic steels of the prior art forcibly deform such soft tissues out of their way, regardless of the soft tissues' back pressure, resulting in far more damage to the soft tissue in the general area of the foreign object sought to be surgically removed.

Wire linkage 12 and/or wire frame 14 may be coated with a material to form a thin, tough, flexible, lubricious coating thereon. One example of such a material is parylene, a synthetic material available from Specialty Coating Systems of Indianapolis, Ind. Alternatively, the inside surfaces of tubular sheath 8 can be modified to reduce drag on wire linkage 12, wire frame 14, and sack 16. In one embodiment of the present invention, the inside surfaces of tubular sheath 8 can be coated with a biocompatible lubricant, such as silicon. Alternatively, the inside surfaces of sheath 8 can be coated with a hydrophylic film.

Figure 6:
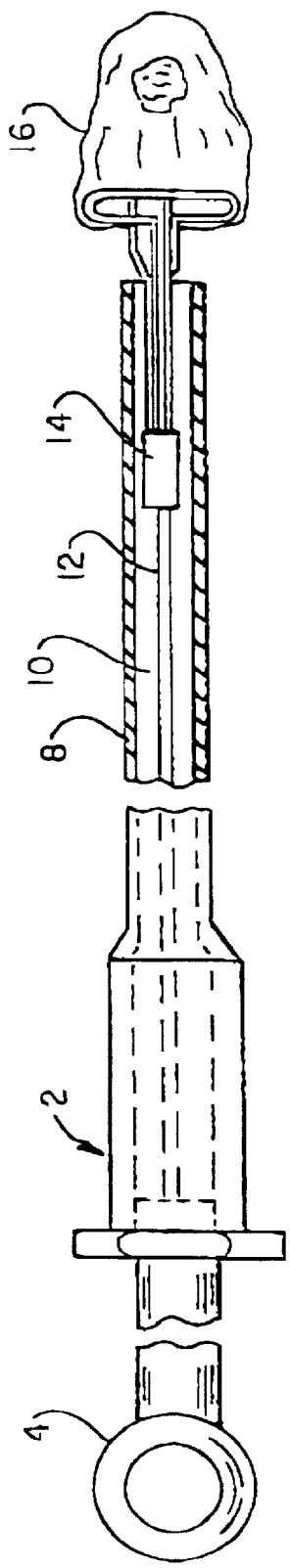
FIG. 6 is a schematic elevational view of the surgical device of the present invention showing a foreign object captured in the sack portion of the device.

Sack 16 as shown in FIGS. 2, 6, 7 and 9 is comprised of any biocompatible material having sufficient strength to ensnare and retain foreign objects within the sack as specifically shown in FIG. 6. In a preferred embodiment, sack 16 is comprised of a polymeric material, and more specifically an elastomeric polyurethane. Other materials of which sack 16 may be formed and which are compatible with the present invention include woven polyester fabrics. In one embodiment of the present invention, the rim of the opening of sack 16 surrounds and is bonded to wire frame 14 to secure sack 16 to wire frame 14. The bonding may be chemical in nature such as with adhesives and the like, or may include heat based bonding, or both. In an alternative embodiment, as shown in FIG. 8, sack 16 may be formed with a series of tab-like projections 24, said tab-like projections being wrapped round half frames 18 and 20 and bonded thereto as described immediately above.

Similar to wire linkage 12 and wire frame 14, sack 16 may also be coated with a material to form a thin, tough, flexible, lubricious coating thereon, and parylene is likewise acceptable for this purpose.

The dimensions of wire frame 14 are determined in most cases by the size of the lumen of the organ, canal or cavity in which the solid object sought to be surgically removed is found. The length of sheath 8 and the length of wire linkage 12 are determined by the position of the organ, canal or cavity, and by the position of the foreign object in the organ, canal or cavity, relative to the surgical entry site available for the operation. Typically, the wire frame 14 is made of wire approximately 0.008 inches in diameter. Typically, the plastic sheath 8 has an outside diameter of 0.039 inches. Its inside diameter is such that it can accommodate the wire frame 14 and sack 16 in their retracted position, as explained below and as shown in FIG. 7.

The surgical device of the present invention is utilized as follows. Utilizing an existing body opening or one surgically created, the surgeon inserts the surgical device of the present invention into the body interior with the wire frame 14 and sack 16 fully retracted into sheath 8 as shown in FIG. 7. Using direct, endoscopic, fluoroscopic, or other visualization, the surgeon manipulates the surgical device of the present invention through the body canals, cavities or organs to a point beyond the foreign object to be removed or captured with respect to the existing or surgical entry point. During this part of the procedure, half frames 18 and 20 are mechanically stretched within their elastic limits within sheath 8 to form respective long narrow loops 26 and 28, the axis of each loop 26 and 28 substantially parallel to the longitudinal axis of wire linkage 12 as shown in FIG. 7. Further, as shown in FIG. 7, sack 16 is additionally retained within sheath 8.

When the surgeon opts to begin the process of removal or capture of the foreign object, the surgeon extends wire linkage 12 and in turn wire frame 14 and sack 16 beyond sheath 8. In the embodiment shown in FIGS. 6 and 7, where handle 2 is of the syringe-type design, the surgeon extends wire frame 14 beyond sheath 8 by pushing plunger 4 inwardly into cylinder 6, whereupon wire linkage 12 causes wire frame 14 to extend beyond sheath 8, whereupon half frames 18 and 20 assume their "learned" super elastic shape within the body canal, cavity or organ in which the surgeon is operating. When half frames 18 and 20 assume their "learned" shapes, the generally perpendicular portions described above are formed, thereby holding sack 16 in an open position coextensive with the circumference of the body lumen. While a surgeon could, for a specific purpose, utilize wire frame 14 to form an opening for sack 16 of a diameter substantially less than that of the body lumen in which the surgeon is operating, in most applications the surgeon will have preselected the wire frame 14 and, more specifically, half frames 18 and 20, to form in their non-retracted state an opening for sack 16 with a diameter which is coextensive, or nearly coextensive, with the body lumen in which the surgeon is operating.

Figure 10:
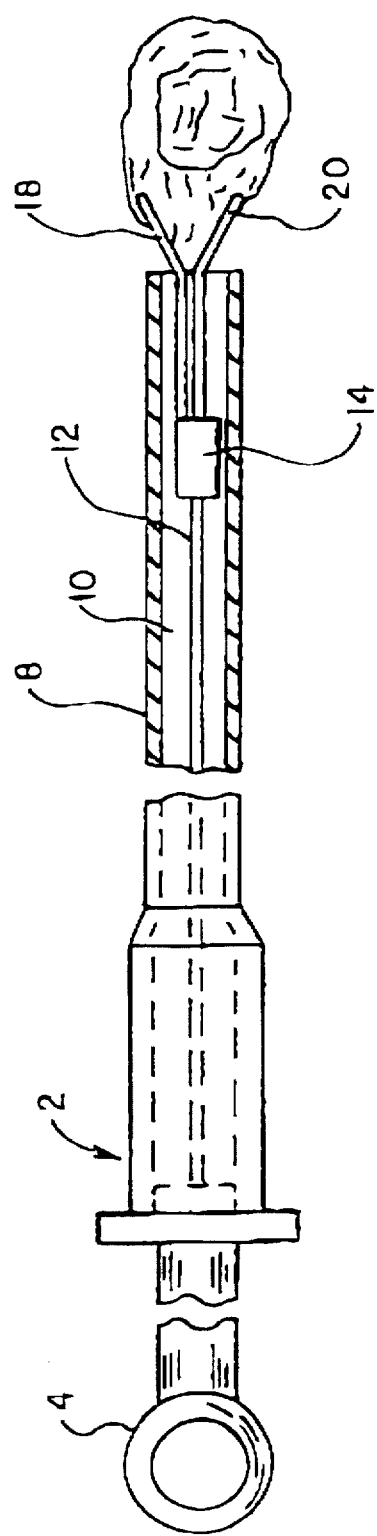
FIG. 10 is a schematic elevational view of the surgical device of the present invention showing a foreign object captured in the sack of the device and with the wire frame of the present invention partially retracted into the sheath of the present invention.

A diameter coextensive with the body lumen is desired because at this point in the operation, the surgeon draws surgical device 1 of the present invention back toward the foreign object to be captured or removed, whereupon the foreign object will be easily captured within the confines of sack 16. Once within the confines of sack 16, the surgeon retracts wire linkage 12 and, in turn, wire frame 14 into sheath 8 to fully encircle and capture the foreign object. In the embodiment shown in FIG. 10, where handle 2 is of the syringe-type design, the surgeon draws plunger 4 outwardly from cylinder 6 causing wire frame 14 and sack 16 to begin to reenter sheath 8 and return to the position as shown in FIG. 7. In many instances the foreign object captured will be of a larger diameter than sheath 8 preventing full retraction of wire frame 14 and sack 16 into sheath 8. In such a case, the surgeon simply draws plunger 4 outwardly from cylinder 6 to a point where the resistance felt, aided by the direct, endoscopic, fluoroscopic, or other visualization, makes it clear to the surgeon that the foreign object is safely retained within sack 16. At that point, the surgeon will then remove the device from the body of the patient with the foreign object safely captured within the confines of sack 16.

As sack 16 is retracted into sheath 8, a bunching of the material of sack 16 has been observed by the present inventors at its interface with sheath 8. Therefore, to avoid this bunching, in a preferred embodiment, sack 16 is formed with a series of one or more cut out portions 30 and 32 as shown in FIG. 9. These cut out portions 30 and 32 avoid the bunching of sack 16 as it is retracted into sheath 8.

Another embodiment of the present invention which avoids the bunching of sack 16 is shown in FIG. 11. As shown in FIG. 11, wire frame 14 includes junction 22, half frame 18 and half frame 20. Wire frame 14 is further fitted with frame members 34 and 36 respectively as shown in FIG. 11. Frame members 34 and 36 differ from half frames 18 and 20 in that they each include an elongated arch 38 and 40 respectively as shown in phantom in FIG. 11. Elongated arches 38 and 40 perform three functions. First, when the device of the present invention is extended so that frame members 34 and 36 extend beyond sheath 8, arches 38 and 40 hold sack 16 in an open position. Second, when the device of the present invention is in its retracted state, as shown in FIG. 11, arches 38 and 40 prevent sack 16 from bunching. Third, when the device of the present invention is extended from the retracted position shown in FIG. 12, arches 38 and 40 operate to push the bottom of sack 16 out of sheath 8, further preventing bunching of sack 16. Frame members 34 and 36 extend along the longitudinal axis of sheath 8 and extend when the assembly is retained within sheath 8 as shown in FIG. 12.

The surgical device of the present invention safely captures and removes foreign objects or excised tissue lodged in body canals, cavities and organs under either direct, endoscopic, fluoroscopic or other visualization. For instance, the present invention may be used to remove calculi from the urinary tract and the common bile duct under endoscopic or fluoroscopic visualization. It may also be used to remove an object forcibly inserted into the ear or nose under direct visualization. It may even be used to retrieve a swallowed object under endoscopic visualization. The device of the present invention is easy to position and requires little manipulation to capture a foreign object lodged in body organs or cavities so as to expedite removal. Further, due to the nature of the firm but pliable shape-memory-effect alloy, minimal trauma will be effected on the tissues surrounding the foreign object to be captured or removed.

To those skilled in the art, many modifications and variations of the present invention are possible in light of the above teachings. It is, therefore, understood that the present invention can be practiced otherwise than as specifically described herein and still will be within the spirit and scope of the appended claims.

We claim:

1. A surgical instrument for removing foreign objects from body canals, cavities or organs, used in minimally invasive procedures performed under either direct, endoscopic, fluoroscopic or other visualization comprising:

a) a handle, said handle including a means for extending and retracting a wire linkage attached to said handle, said wire linkage having a first proximal end attached to said means for extending and retracting said wire linkage, said wire linkage having a second distal end;

b) an elongated tubular sheath attached to said handle, said sheath having a hollow lumen extending longitudinally therethrough, said wire linkage contained within said lumen, said wire linkage being adapted to slide within said lumen of said sheath;

c) a wire frame attached to said wire linkage at said second distal end of said wire linkage, said wire frame being extendible beyond said sheath and retractable into said sheath by said means for extending and retracting said wire linkage which correspondingly extends and retracts said wire frame within said sheath, said wire frame being formed of a shape-memory-effect alloy wire, said alloy in a super elastic state and previously trained to form at an end of the wire frame opposite said wire linkage at least a partial loop, said at least partial loop forming when said wire frame is extended beyond said sheath, said at least partial loop being continuous between the ends of each of said at least two control arms opposite the wire linkage said wire frame having at least two control arms diverging from the longitudinal axis of said sheath between said wire linkage and said at least partial loop when said wire frame is extended beyond said sheath, said at least two control arms positioned parallel to and adjacent the longitudinal axis of the sheath when said wire frame is retracted into said sheath; and d) a sack having a mouth, said mouth of said sack being attached to said wire frame wherein
   said mouth of said sack is opened and closed when said at least two control arms are extended from and retracted into said sheath.

2. The surgical instrument of claim 1 wherein said handle is a syringe-type handle and said means for extending and retracting said wire linkage includes a plunger and cylinder, said plunger sized to slide within said cylinder, said first proximal end of said wire linkage being attached to said plunger and wherein said sheath is attached to said cylinder.

3. The surgical instrument of claim 1 wherein said handle is a pistol-type handle and said means for extending and retracting said wire linkage includes a trigger assembly, wherein said wire linkage is attached to said trigger assembly.

4. The surgical instrument of claim 1 wherein the plane of said loop is approximately perpendicular to the longitudinal axis of said sheath.

5. The surgical instrument of claim 1 wherein said wire frame is composed of a biocompatible material.

6. The surgical instrument of claim 1 wherein said wire frame is made of a biocompatible shape-memory-effect alloy in its super elastic state.

7. The surgical instrument of claim 1 wherein said wire linkage is made of a biocompatible metal or alloy.

8. The surgical instrument of claim 1 wherein said shape-memory-effect alloy is Nitinol.

9. The surgical instrument of claim 1 wherein at least one of said wire frame and said wire linkage is coated with a flexible biocompatible film.

10. The surgical instrument of claim 9 wherein said film is parylene.

11. The surgical instrument of claim 1 wherein said sack is coated with a flexible biocompatible film.

12. The surgical instrument of claim 11 wherein said film is parylene.

13. The surgical instrument of claim 1 wherein said sheath is composed of a plastic material.

14. The surgical instrument of claim 1 wherein said sheath is composed of flexible, biocompatible polyester.

15. The surgical instrument of claim 1 wherein said shape-memory-effect alloy wire is solid wire.

16. The surgical instrument of claim 1 wherein said shape-memory-effect alloy wire is stranded wire.

17. The surgical instrument of claim 1 wherein said wire frame is further comprised of a first half frame and a second half frame, wherein said first half frame and said second half frame are joined at a junction and wherein said junction is attached to said wire linkage.

18. The surgical instrument of claim 17 wherein said first and said second half frame respectively each further include an attached frame member disposed along the longitudinal axis of said sheath, wherein said frame members operate to prevent bunching of said sack during extension of said wire frame from said sheath.

19. The surgical instrument of claim 1 wherein said sack is comprised of a woven polyester fabric.

20. The surgical instrument of claim 1 wherein said sack is comprised of an elastomeric polyurethane.

21. The surgical instrument of claim 1 wherein said sack includes a plurality of tabs, wherein said tabs are folded around said wire frame and are bonded to said wire frame to secure said sack to said wire frame.

22. The surgical instrument of claim 1 wherein said sack includes at least one cut out portion about said mouth of said sack where said sack is attached to said wire frame, wherein said cut out portion prevents bunching of said sack as said sack is retracted into said sheath.

23. A method of removing a foreign object from a body canal, cavity or organ, comprising the steps of:

a) inserting a surgical instrument into said body canal, cavity or organ through an entry point, said entry point including at least one of an existing body opening and a surgically created body opening;

b) viewing the inserting of said surgical instrument through at least one of the group consisting of direct examination, endoscopic examination, or fluoroscopic examination;

c) continuing the inserting of said surgical instrument to a point beyond said foreign object with respect to entry point;

d) extending said surgical instrument to form a sack;

e) withdrawing said surgical instrument to encircle said foreign object within said sack;

f) retracting said surgical instrument to capture said foreign object in said sack;

g) removing said surgical instrument and said foreign object from said body, wherein said surgical instrument includes i) a handle, said handle including a means for extending and retracting a wire linkage attached to said handle, said wire linkage having a first proximal end attached to said means for extending and retracting said wire linkage, said wire linkage having a second distal end;

ii) an elongated tubular sheath attached to said handle, said sheath having a hollow lumen extending longitudinally therethrough, said wire linkage contained within said lumen, said wire linkage being adapted to slide within said lumen of said sheath;

iii) a wire frame attached to said wire linkage at said second distal end of said wire linkage, said wire frame being extendible beyond said sheath and retractable into said sheath by said means for extending and retracting said wire linkage which correspondingly extends and retracts said wire frame within said sheath, said wire frame being formed of a shape-memory-effect alloy wire, said alloy in a super elastic state and previously trained to form at an end of the wire frame opposite said wire linkage at least a partial loop, said at least partial loop forming when said wire frame is extended beyond said sheath, said at least partial loop being continuous between the ends of each of said at least two control arms opposite the wire linkage said wire frame having at least two control arms diverging from the longitudinal axis of said sheath between said wire linkage and said at least partial loop when said wire frame is extended beyond said sheath, said at least two control arms positioned parallel to and adjacent the longitudinal axis of the sheath when said wire frame is retracted into said sheath; and iv) a sack having a mouth, said mouth of said sack being attached to said wire frame, wherein said mouth of said sack is opened and closed when said at least two control arms are extended from and retracted into said sheath.

* * * * *

UNITED STATES PATENT AND TRADEMARK OFFICE
CERTIFICATE OF CORRECTION

PATENT NO. : 5,779,716
DATED : July 14, 1998
INVENTOR(S) : Gerald G. Cano and Robert W. Doebler It is certified that error appears in the above-identified patent and that said Letters Patent is hereby corrected as shown below:

Claim 1, Column 8 Lines 45-47, delete --said at least partial loop being continuous between the ends of each of said at least two control arms opposite the wire linkage--.

Claim 1, Column 8 Line 51, after "sheath," insert --said at least partial loop being continuous between the ends of each of said at least two control arms opposite the wire linkage,--.

Claim 23, paragraph (g)(iii), Column 10 Lines 41-43, delete --said at least partial loop being continuous between the ends of each of said at least two control arms opposite the wire linkage--.

Claim 23, paragraph (g)(iii), Column 10 Line 47, after "sheath," insert --said at least partial loop being continuous between the ends of each of said at least two control arms opposite the wire linkage,--.

Signed and Sealed this

Twenty-seventh Day of June, 2000

Attest:

Q. TODD DICKINSON

*Attesting Officer*  *Director of Patents and Trademarks*